(12) United States Patent
Park et al.

(10) Patent No.: US 8,805,621 B2
(45) Date of Patent: Aug. 12, 2014

(54) APPARATUS AND METHOD FOR COMPARING PROTEIN STRUCTURE USING 3D RDA AND FOURIER DESCRIPTOR

(75) Inventors: Chan-Yong Park, Daejon (KR); Sung-Hee Park, Daejon (KR); Dae-Hee Kim, Daejon (KR); Soo-Jun Park, Seoul (KR); Seon-Hee Park, Daejon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1 day.

(21) Appl. No.: 11/928,672

(22) Filed: Oct. 30, 2007

(65) Prior Publication Data
US 2008/0140659 A1    Jun. 12, 2008

(30) Foreign Application Priority Data

Dec. 6, 2006 (KR) .................. 10-2006-0123349

(51) Int. Cl.
  *G01N 31/00* (2006.01)
  *G06F 19/16* (2011.01)
  *G06F 19/10* (2011.01)
(52) U.S. Cl.
  CPC ............... *G06F 19/16* (2013.01); *G06F 19/10* (2013.01)
  USPC .............................................. 702/27; 702/19
(58) Field of Classification Search
  CPC .................................. G06F 19/10; G06F 19/16
  See application file for complete search history.

(56) References Cited

U.S. PATENT DOCUMENTS

| 5,353,236 | A | 10/1994 | Subbiah |
| 5,557,535 | A | 9/1996 | Srinivasan et al. |
| 6,813,615 | B1 | 11/2004 | Colasanti et al. |
| 2003/0143628 | A1 | 7/2003 | Onizuka |
| 2003/0215877 | A1 * | 11/2003 | Love et al. ............ 435/7.1 |

FOREIGN PATENT DOCUMENTS

| KR | 10-2003-0005318 | 1/2003 |
| KR | 20050046960 | 5/2005 |
| KR | 10-2006-0070300 | 6/2006 |

OTHER PUBLICATIONS

L. Holm, et al., "Protein Structure Comparison by Alignment of Distance Matrices," J. Mol. Biol, 233, 1993, pp. 123-138.
A. P. Singh, et al., "Hierarchical Protein Structure Superposition Using Both Secondary Structure and Atomic Representations" In Proceedings, Intl. Conf. on Intelligent Systems in Molecular Biology, pp. 284-293, 1997.

* cited by examiner

*Primary Examiner* — Michael Borin
(74) *Attorney, Agent, or Firm* — Rabin & Berdo, P.C.

(57) ABSTRACT

Provided is an apparatus and method for comparing a protein structure, which can search a protein similar to an inquiry protein in a 3D protein database in real time by describing a feature of a protein structure by using a three-dimensional (3D) relative directional angle (RDA) and a Fourier descriptor. The apparatus includes: a 3D RDA coder configured to code a 3D RDA of a target protein data or an inquiry protein data inputted from the outside; a Fourier transformer configured to obtain Fourier coefficients by Fourier transforming 3D RDA coding values coded by the 3D RDA coder; a comparator configured to compare the obtained Fourier coefficient of the target protein data with the obtained Fourier coefficient of the inquiry protein data; and a data generator configured to output protein data in order from high similarity to low similarity according to the comparison result of the comparator.

3 Claims, 4 Drawing Sheets

APPARATUS AND METHOD FOR COMPARING PROTEIN STRUCTURE USING 3D RDA AND FOURIER DESCRIPTOR

CROSS-REFERENCE(S) TO RELATED APPLICATIONS

The present invention claims priority of Korean Patent Application No. 10-2006-0123349, filed on Dec. 6, 2006, which is incorporated herein by reference.

BACKGROUND OF THE INVENTION

1. Field of the Invention

The present invention relates to an apparatus and method for comparing a protein structure, which can search a similar protein in a protein database such as a protein data bank (PDB) database; and, more particularly, to an apparatus and method for comparing a protein structure, which can search a protein similar to an inquiry protein in a 3D protein database in real time by describing a feature of a protein structure by using a three-dimensional (3D) relative directional angle (RDA) and a Fourier descriptor.

This work was supported by the Information Technology (IT) research and development program of the Korean Ministry of Information and Communication (MIC) and/or the Korean Institute for Information Technology Advancement (IITA) [2005-S-008-02, "SW Component Development of Bio Data Mining & Integrated Management"].

2. Description of Related Art

Generally, a protein database stores more than 25,000 kinds of proteins. About 100 protein data are added in one week. Thus, additional cost for classifying and searching proteins is always incurred.

There are two methods for comparing similar proteins.

The first method is a pairwise 3D structure comparison method. The pairwise 3D structure comparison method is used to express a similarity of two 3D protein structures in a quantitative value. The pairwise 3D structure comparison is called a 3D structure matching or alignment. Generally, a 3D alignment problem is known as NP-complete. The 3D structure problem has been solved using heuristic methods. The methods measure use different calculation methods to measure a score of the similarity.

The second method is to search a protein similar to an inquiry protein in a database. Generally, the second method shows M results (where M is a natural number) having a score equal to or greater than a threshold value. In this case, since the search is performed on all data of the protein database, N-time comparing processes are required for searching the protein in N databases (where N is a natural number. As the size of the protein database increases, the efficiency of data search is gradually degraded. Therefore, a fast database search becomes an important factor.

The conventional pairwise 3D structure comparison includes a sequential structure alignment program (SSAP), a distance alignment tool (DALI), a vector alignment search tool (VAST), and a combinatorial extension (CE). Most of these conventional methods are performed through two alignment steps. The first alignment step is to fine a similarity of a secondary structure element or a Cα backbone fragment, and the second alignment step is to align Cα atoms. Although these conventional methods provide very good results in view of similarity, they have a very slow response time when searching the protein database.

Although Topscan and SCALE are the pairwise 3D structure comparison method, they use only the secondary structure element. Since the two methods do not perform the second alignment step, their search speed is faster than SSAP, DALI, VAST, and CE. However, the two methods have disadvantages in that their search results are very incorrect and their response time is too slow to use them as the search method in a large-scale protein database.

In addition, the response time of Guerra, protein structure indexing (PSI), and ProtDex is also too slow to use them as the search method in a large-scale protein database.

SUMMARY OF THE INVENTION

An embodiment of the present invention is directed to providing an apparatus and method for comparing a protein structure, which can search a protein similar to an inquiry protein in a 3D protein database in real time by describing a feature of a protein structure by using a 3D RDA and a Fourier descriptor.

In accordance with an aspect of the present invention, there is provided an apparatus for comparing a protein structure using a three-dimensional relative directional angle (3D RDA) and a Fourier descriptor, which includes: a 3D RDA coder configured to code a 3D RDA of a target protein data or an inquiry protein data inputted from the outside; a Fourier transformer configured to obtain Fourier coefficients by Fourier transforming 3D RDA coding values coded by the 3D RDA coder; a comparator configured to compare the obtained Fourier coefficient of the target protein data with the obtained Fourier coefficient of the inquiry protein data; and a data generator configured to output protein data in order from high similarity to low similarity according to the comparison result of the comparator.

In accordance with another aspect of the present invention, there is provided a method for comparing a protein structure using a three-dimensional relative directional angle (3D RDA) and a Fourier descriptor, which includes the steps of: a) coding a 3D RDA of a target protein data or an inquiry protein data inputted from the outside; b) obtaining Fourier coefficients by Fourier transforming 3D RDA coding values; c) comparing the obtained Fourier coefficient of the target protein data with the obtained Fourier coefficient of the inquiry protein data; and d) outputting protein data in order from high similarity to low similarity according to the comparison result of the comparator.

After the protein is expressed with a Fourier coefficient and stored in the database, the Fourier coefficient of the inquiry protein is compared with the Fourier coefficient of the protein stored in the database. Therefore, the search speed is very fast and the identical proteins and the similar proteins can be searched in real time because the approximation of the input data is performed due to the characteristic of the Fourier transform.

Furthermore, after the target protein is expressed with the Fourier coefficient, the Fourier coefficient of the inquiry protein is compared with the Fourier coefficient of the target protein. Therefore, the search speed is very fast and the identical proteins and the similar proteins can be searched in real time because the approximation of the input data is performed due to the characteristic of the Fourier transform.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

DESCRIPTION OF SPECIFIC EMBODIMENTS

The advantages, features and aspects of the invention will become apparent from the following description of the embodiments with reference to the accompanying drawings, which is set forth hereinafter.

Figure 1:
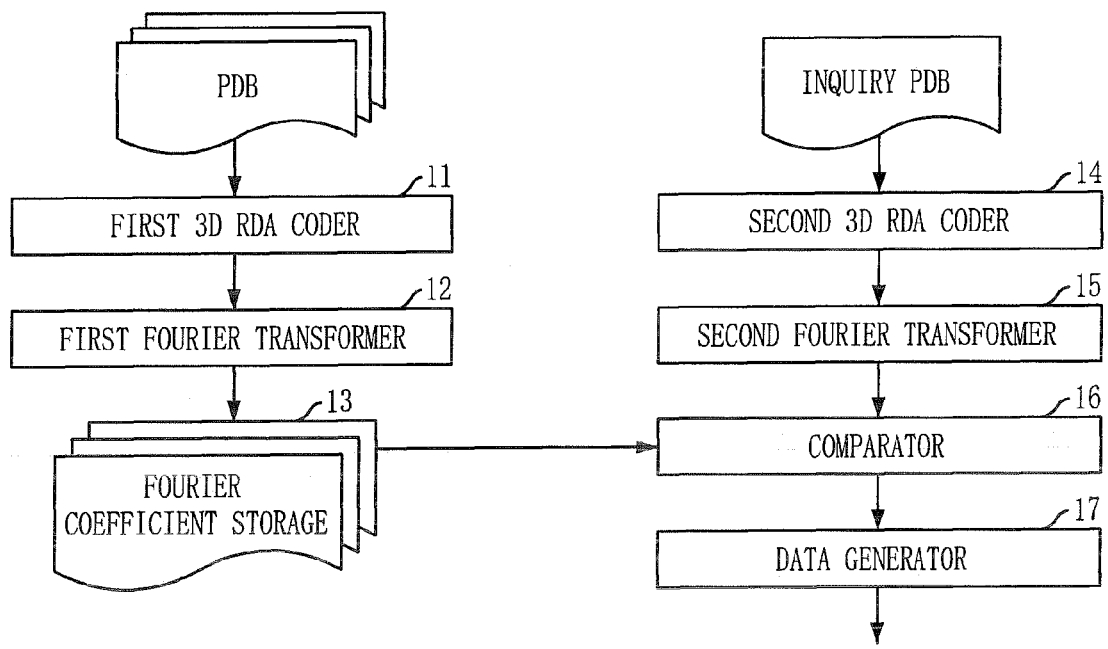
FIG. 1 is a block diagram of an apparatus for comparing a protein structure using a 3D RDA and a Fourier descriptor in accordance with an embodiment of the present invention.

FIG. 1 is a block diagram of an apparatus for comparing a protein structure using a 3D RDA and a Fourier descriptor in accordance with an embodiment of the present invention.

Referring to FIG. 1, the protein comparing apparatus includes a first 3D RDA coder 11, a first Fourier transformer 12, a Fourier coefficient storage 13, a second 3D RDA coder 14, a second Fourier transformer 15, a comparator 16, and a data generator 17. The first 3D RDA coder 11 codes a 3D RDA of a target protein data provided from a protein data bank (PDB) database, which is a protein database. The first Fourier transformer 12 obtains Fourier coefficients by Fourier transforming 3D RDA coding values coded by the first 3D RDA coder 11. The Fourier coefficient storage 13 stores the Fourier coefficient obtained by the first Fourier transformer 12. The second 3D RDA coder 14 codes a 3D RDA of an inquiry protein data inputted from the outside, e.g., a user. The second Fourier transformer 15 obtains Fourier coefficients by Fourier transforming 3D RDA coding values coded by the second 3D RDA coder 14. The comparator 16 compares the Fourier coefficient stored in the Fourier coefficient storage 13 with the Fourier coefficient obtained by the second Fourier transformer 15. The data generator 17 outputs protein data in order from high similarity to low similarity according to the comparison result of the comparator 16.

As another embodiment of the present invention, the Fourier coefficient storage 13 may not be provided in the protein comparing apparatus. In this case, the Fourier coefficient can be directly transferred from the first Fourier transformer 12 to the comparator 16.

It is desirable that the Fourier coefficient storage 13 is implemented in a database form, and the comparator 16 is configured to search the Fourier coefficient stored in the Fourier coefficient storage 13 by using the Fourier coefficient obtained by the second Fourier transformer 15.

Figure 2:
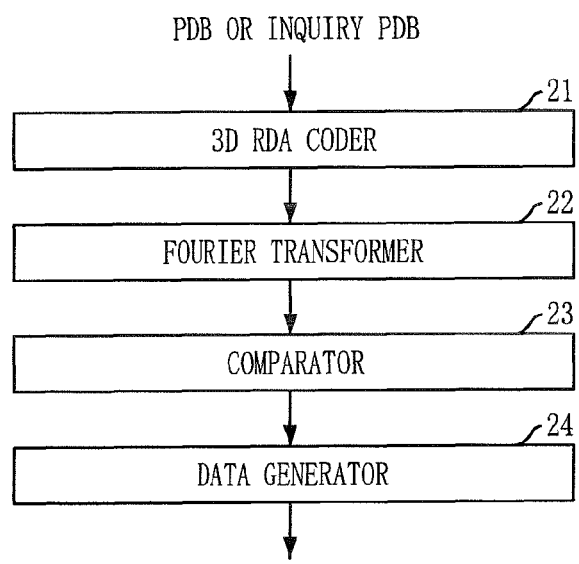
FIG. 2 is a block diagram of an apparatus for comparing a protein structure using a 3D RDA and a Fourier descriptor in accordance with another embodiment of the present invention.

FIG. 2 is a block diagram of an apparatus for comparing a protein structure using a 3D RDA and a Fourier descriptor in accordance with another embodiment of the present invention.

Referring to FIG. 2, the protein comparing apparatus includes a 3D RDA coder 21, a Fourier transformer 22, a comparator 23, and a data generator 24. The 3D RDA coder 21 codes a 3D RDA of a target protein data or an inquiry protein data, which is inputted from the outside. The Fourier transformer 22 obtains Fourier coefficients by Fourier transforming 3D RDA coding values coded by the 3D RDA coder 21. The comparator 23 compares the obtained Fourier coefficient of the target protein data with the obtained Fourier coefficient of the inquiry protein data. The data generator 24 outputs protein data in order from high similarity to low similarity according to the comparison result of the comparator 23.

In this embodiment, a Fourier coefficient storage (not shown) may be further provided for storing the Fourier coefficient of the target protein data, which is obtained by the Fourier transformer 22, and the comparator 23 may be configured to compare the Fourier coefficient of the target protein data, which is stored in the Fourier coefficient storage (not shown), with the Fourier coefficient of the inquiry protein data, which is obtained by the Fourier transformer 22.

It is desirable that the Fourier coefficient storage is implemented in a database form, and the comparator 23 is configured to search the Fourier coefficient stored in the Fourier coefficient storage by using the Fourier coefficient obtained by the second Fourier transformer 22.

The protein comparing apparatus will be described in more detail with reference to FIGS. 1 and 2.

Figure 3:
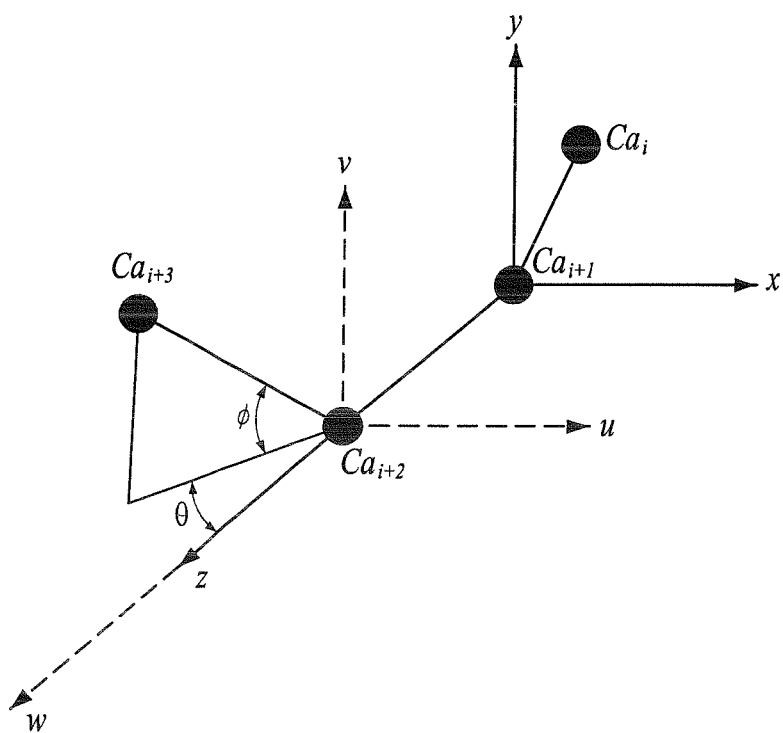
FIG. 3 is a graph illustrating a 3D RDA coding in accordance with an embodiment of the present invention.

The 3D RDA coding is performed on Cα atoms constructing the backbone of protein and codes the 3D RDA. The 3D RDA is translation and rotation invariant feature and the RDA is coded into $(\theta, \phi)$). The coding is performed on the entire backbone of protein to obtain $\{(\theta_1, \phi_1), (\theta_2, \phi_2), (\theta_2, \phi_2), \ldots, (\theta_n, \phi_n)\}$. An example of a coding on $C\alpha_i$, $C\alpha_{i+1}$, $C\alpha_{i+2}$, $C\alpha_{i+3}$ is illustrated in FIG. 3. As expressed in Eq. 1 below, after four atoms are transformed into uvw coordinate, a uvw coordinate of $C\alpha_{i+3}$ is obtained. Then, a $(\theta, \phi)$ value is obtained by transforming the uvw coordinate into a spherical coordinate.

$$\text{Transformed Coordinate } u, v, w \qquad \text{Eq. 1}$$
$$w = \overline{C\alpha_{i+2}} - \overline{C\alpha_{i+1}}$$
$$v' = \overline{C\alpha_i} - \overline{C\alpha_{i+1}}$$
$$u = \vec{v'} \times \vec{w}$$
$$v = \vec{u} \times \vec{w}$$
$$\text{Transformed Coordinate of } C\alpha_{i+3}(x, y, z): C\alpha'_{i+3}(x', y', z')$$
$$x' = u \cdot C\alpha_{i+3}(x, y, z)$$
$$y' = v \cdot C\alpha_{i+3}(x, y, z)$$
$$z' = w \cdot C\alpha_{i+3}(x, y, z)$$
$$RDA(\theta, \phi)$$
$$\theta = \tan^{-1}\left(\frac{x'}{z'}\right), \quad \varphi = \sin^{-1}\left(\frac{y'}{r}\right)$$

$\{(\theta_1, \phi_1), (\theta_2, \phi_2), (\theta_3, \phi_3), \ldots, (\theta_n, \phi_n)\}$ is Fourier transformed to obtain a Fourier coefficient a(u). The Fourier coefficient a(u) is generally expressed as a complex number. Therefore, a power spectrum value of the Fourier coefficient a(u) is used as an actual comparison value.

$$P(u,v)=|a(u)|\times|a(u)|=R^2(u,v)+I^2(u,v) \qquad \text{Eq. 2}$$

Eq. 2 is a general equation for calculating the power spectrum of the Fourier coefficient a(u). In Eq. 2, R stands for a real term of the Fourier coefficient a(u), and I stands for an imaginary term of the Fourier coefficient a(u). The power spectrum (P(u,v)) of the Fourier coefficient a(u) can be obtained by adding a real term square ($R^2$ (u,v)) to an imaginary term square ($I^2$ (u,v)).

An inverse Fourier transform of a Fourier coefficient a(u) of Eq. 3 is expressed as s(k) of Eq. 4 below. If only P Fourier coefficients (where P is a natural number) are used, the result is expressed as ŝ(k) of Eq. 5. ŝ(k) is expressed as an approximate value of s(k).

$$a(u) = \sum_{k=0}^{K-1} s(k)e^{-j2\pi uk/K} \qquad \text{Eq. 3}$$

where K represents a size of data to be frequency transformed.

$$s(k) = \frac{1}{K} \sum_{u=0}^{K-1} a(u)e^{j2\pi uk/K} \qquad \text{Eq. 4}$$

$$\hat{s}(k) = \frac{1}{P} \sum_{u=0}^{P-1} a(u)e^{j2\pi uk/K} \qquad \text{Eq. 5}$$

An operation of the protein comparing apparatus in accordance with the embodiment of the present invention will be described below with reference to FIGS. 4 and 5. Since the detailed embodiment has been described above, only a brief operation flow will be described below.

Figure 4:
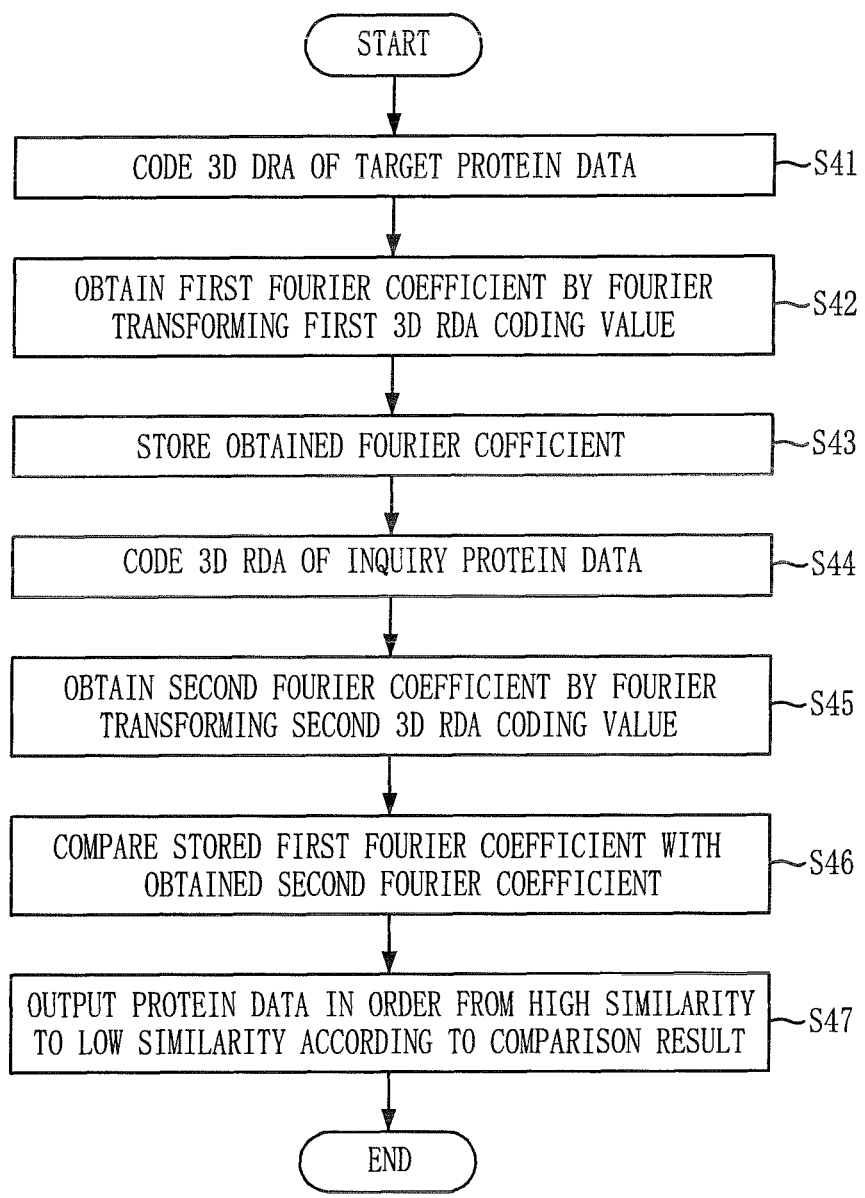
FIG. 4 is a flowchart illustrating a method for comparing a protein structure using a 3D RDA and a Fourier descriptor in accordance with an embodiment of the present invention.

FIG. 4 is a flowchart illustrating a method for comparing a protein structure using a 3D RDA and a Fourier descriptor in accordance with an embodiment of the present invention.

In step S41, the first 3D RDA coder 11 codes a 3D RDA of a target protein data provided from a PDB database, which is a protein database.

In step S42, the first Fourier transformer 12 obtains a Fourier coefficient by Fourier transforming 3D RDA coding values coded by the first 3D RDA coder 11.

In step S43, the Fourier coefficient storage 13 stores the Fourier coefficient obtained by the first Fourier transformer 12.

In step S44, the second 3D RDA coder 14 codes a 3D RDA of an inquiry protein data inputted from the outside, e.g., a user.

In step S45, the second Fourier transformer 15 obtains Fourier coefficients by Fourier transforming 3D RDA coding values coded by the second 3D RDA coder 14.

In step S46, the comparator 16 compares the Fourier coefficient stored in the Fourier coefficient storage 13 with the Fourier coefficient obtained by the second Fourier transformer 15.

In step S47, the data generator 17 outputs protein data in order from high similarity to low similarity according to the comparison result of the comparator 16.

As another embodiment of the present invention, the step S43 of storing the Fourier coefficient may not be performed. In this case, the Fourier coefficient obtained by the first Fourier transformer 12 is directly used in the step S46 of comparing the Fourier coefficients.

Figure 5:
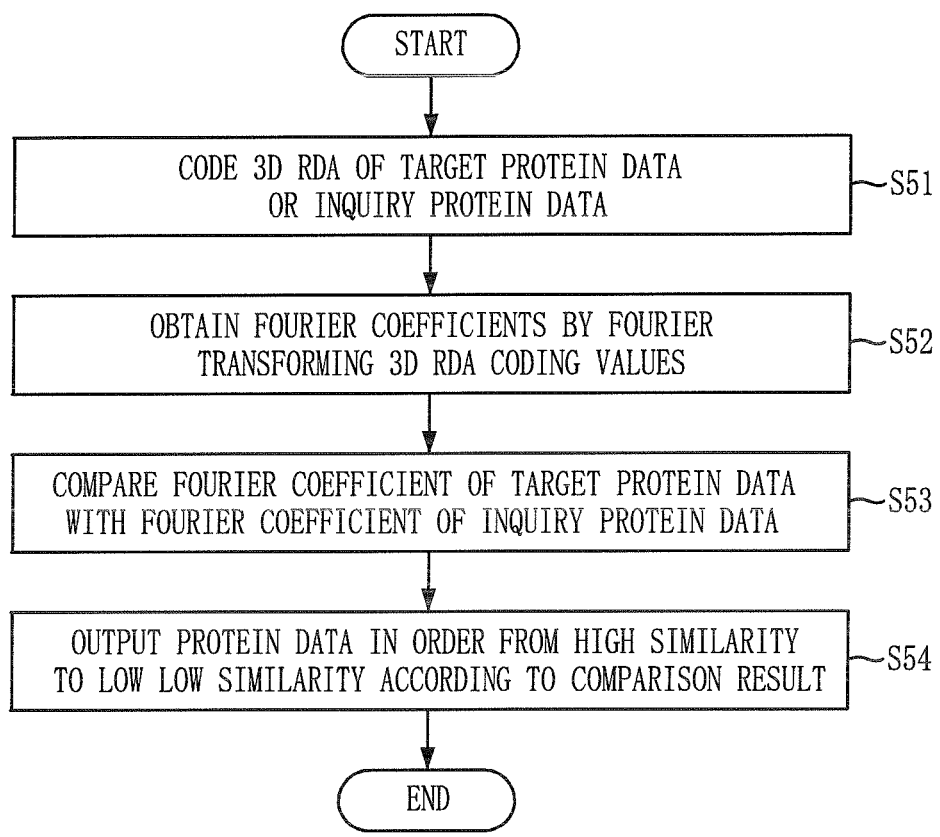
FIG. 5 is a flowchart illustrating a method for comparing a protein structure using a 3D RDA and a Fourier descriptor.

FIG. 5 is a flowchart illustrating a method for comparing a protein structure using a 3D RDA and a Fourier descriptor.

In step S51, the 3D RDA coder 21 codes a 3D RDA of a target protein data or an inquiry protein data, which is inputted from the outside.

In step S52, the Fourier transformer 22 obtains Fourier coefficients by Fourier transforming 3D RDA coding values coded by the 3D RDA coder 21.

In step S53, the comparator 23 compares the obtained Fourier coefficient of the target protein data with the obtained Fourier coefficient of the inquiry protein data.

In step S54, the data generator 24 outputs protein data in order from high similarity to low similarity according to the comparison result of the comparator 23.

In this embodiment, the method may further include the step of storing the Fourier coefficient of the target protein data, which is obtained by the Fourier transformer 22, and the comparator 23 may be configured to compare the Fourier coefficient of the target protein data, which is stored in the step of storing the Fourier coefficient, with the Fourier coefficient of the inquiry protein data, which is obtained by the Fourier transformer 22.

As described above, the apparatus and method for comparing the protein structure in accordance with the embodiments of the present invention can search the protein similar to the inquiry protein in the 3D protein database in real time by describing the feature of the protein structure by using the 3D RDA and the Fourier descriptor.

Further, similar proteins can be classified and biological evidence of protein evolution can be found.

After the protein is expressed with a Fourier coefficient and stored in the database, the Fourier coefficient of the inquiry protein is compared with the Fourier coefficient of the protein stored in the database. Alternatively, after the target protein is expressed with the Fourier coefficient, the Fourier coefficient of the inquiry protein is compared with the Fourier coefficient of the target protein. Therefore, the search speed is very fast and the identical proteins and the similar proteins can be searched in real time because the approximation of the input data is performed due to the characteristic of the Fourier transform.

The methods in accordance with the embodiments of the present invention can be realized as programs and stored in a computer-readable recording medium that can execute the programs. Examples of the computer-readable recording medium include CD-ROM, RAM, ROM, floppy disks, hard disks, magneto-optical disks and the like.

While the present invention has been described with respect to the specific embodiments, it will be apparent to those skilled in the art that various changes and modifications may be made without departing from the spirit and scope of the invention as defined in the following claims.

What is claimed is:

1. A method for searching, among a plurality of target protein data saved in a protein database, a similar protein data that is structurally similar to an inquiry protein data inputted from the outside, comprising the steps of:
   a) respectively coding three-dimensional relative directional angles (3D RDAs) of the target protein data, and coding a 3D RDA of the inquiry protein data, wherein the coding comprises transforming three-dimensional coordinates of the target protein data into spherical coordinates of the target protein data;
   b) respectively obtaining a Fourier coefficient of each of the plurality of target protein data by Fourier transforming 3D RDA coding values of the target protein data, and obtaining a Fourier coefficient of the inquiry protein data by Fourier transforming a 3D RDA coding value of the inquiry protein data, wherein the transforming comprises transforming the spherical coordinates obtained in the step a);
   c) comparing the Fourier coefficients of the target protein data with the Fourier coefficient of the inquiry protein data; and d) outputting the target protein data in structurally similar order in regard to the inquiry protein data based on result of the comparison, and searching the similar protein data among the target protein data outputted in structurally similar order, wherein the steps a), b), c) and d) are performed by a sufficiently programmed computer.

2. The method of claim 1, further comprising the step:

e) storing the Fourier coefficients of the target protein data;

wherein the step c) compares the stored Fourier coefficients of the target protein data with the Fourier coefficient of the inquiry protein data.

3. The method of claim 1, wherein the step c) includes the step:

c1) calculating power spectrums of the target protein data by respectively adding a real term square to an imaginary term square in regard to each of the Fourier coefficients of the target protein data; and c2) calculating power spectrum of the inquiry protein data by adding a real term square to an imaginary term square in regard to the Fourier coefficient of the inquiry protein data.

\* \* \* \* \*